(12) United States Patent
Camden

(10) Patent No.: US 6,384,049 B1
(45) Date of Patent: May 7, 2002

(54) CANCER TREATMENT

(75) Inventor: James Berger Camden, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/578,281

(22) Filed: May 25, 2000

(51) Int. Cl.$^7$ ................................ A61K 31/44
(52) U.S. Cl. ....................... 514/303; 514/8; 514/12; 424/450
(58) Field of Search ............... 514/303, 8, 12; 424/450

(56) References Cited

U.S. PATENT DOCUMENTS

| | | | |
|---|---|---|---|
| 3,590,045 A | | 6/1971 | Vogt |
| 5,767,138 A | * | 6/1998 | Camden ............ 514/365 |
| 6,093,728 A | * | 7/2000 | McMahon et al. ...... 514/303 |

FOREIGN PATENT DOCUMENTS

GB    1 318 859    5/1973

OTHER PUBLICATIONS

Chemical Abstracts 93:39290, "The antifungal activity of alkyl benzimidazol–2–carbamates and related compounds" (1979).*

Printout for chemical structure of Chemical Registry Number 33259–74–4.*

* cited by examiner

*Primary Examiner*—Frederick Krass
(74) *Attorney, Agent, or Firm*—Bart S. Hersko

(57) ABSTRACT

This invention is a method of treating cancer, including carcinomas and sarcomas through the administration of a pharmaceutical composition containing a pyridinylimidazole carbamate. The pyridinylimidazole carbamate is selected from the group consisting of:

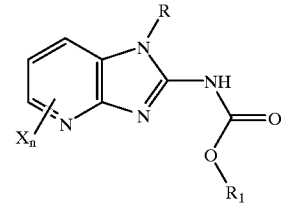

wherein X is independently selected from the group consisting of halo, for example, bromo, fluoro, chloro, iodo; hydroxyl, alkyl of less than 8 carbon atoms or alkoxy of less than 8 carbon atoms; n is a positive integer less than 4; R is hydrogen or an alkyl group of from 1 to 8 carbons and its pharmaceutically acceptable salts and prodrugs thereof.

24 Claims, No Drawings

CANCER TREATMENT

TECHNICAL FIELD

A method of treating cancer, including carcinomas and sarcomas, with a pyridinylimidazole carbamate is provided. The pharmaceutical composition containing pyridinylimidazole carbamate is also claimed.

BACKGROUND OF THE INVENTION

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

The development of materials that would target tumor cells due to some unique specificity for them would be a breakthrough. Alternatively, materials that were cytotoxic to tumor cells while exerting mild effects on normal cells is also desirable.

Carbendazim, a benzimidazole carbamate, has been studied as a cancer treatment. See U.S. Pat. No. 5,767,138 issued Jun. 16, 1998 to J. B. Camden.

It has been found that pyridinylimidazole carbamates can be used to treat cancer. Alkyl pyridinylimidazole carbamate has been used as an anthelmintic (See GB 1,318,859 and U.S. Pat. No. 3,590,045.)

SUMMARY OF THE INVENTION

Claimed herein is a method of treating cancer, in particular, treating cancers in warm blooded animals and humans, comprising administering a therapeutically effective amount of a composition comprising one or more pyridinylimidazole carbamate compounds selected from the group consisting of:

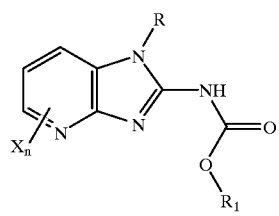

wherein X is independently selected from the group consisting of halo, for example, bromo, fluoro, chloro, iodo; hydroxyl, alkyl of less than 8 carbon atoms or alkoxy of less than 8 carbon atoms; n is a positive integer less than 4; and R or $R_1$ are independently selected from hydrogen or an alkyl group of from 1 to 8 carbons and its pharmaceutically acceptable salts and prodrugs thereof. Preferably $R_1$ is an alkyl group of less than 3 carbon atoms, the preferred compounds are pyridinylimidazole carbamate wherein X is hydrogen, methyl or ethyl and R is methyl or hydrogen and $R_1$ is methyl or ethyl.

Preferably the compound is imidazo [4,5-b]pyridine-2-carbamic acid, methyl ester which has the formula:

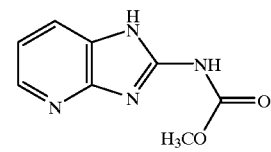

The present invention also provides a pharmaceutical composition comprising a pharmaceutically acceptable carrier and a therapeutically effective amount of a pyridinylimidazole carbamate.

These compositions have been discovered to inhibit the growth of cancer or other tumors in humans or animals by administration of a therapeutically effective amount of the composition, preferably by administering pyridinylimidazole carbamate to the site of the cancer.

More specifically, this invention provides an anti-cancer composition comprising a pharmaceutical carrier and pyridinylimidazole carbamate as defined herein along with a method for treating such cancers. The composition can be used in conjunction with other chemotherapeutic agents and other cancer treatments.

DETAILED DESCRIPTION OF THE INVENTION

A. Definitions:

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" is salt of the pyridinylimidazole carbamate which has been modified by making acid or base salts of the compounds. Examples of pharmaceutically acceptable salts include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, a "pharmaceutical carrier" is a pharmaceutically acceptable solvent, suspending agent or vehicle, for delivering the pyridinylimidazole carbamate to the animal or human. The carrier may be liquid or solid and is selected with the planned manner of administration in mind. Liposomes are also a pharmaceutical carrier.

As used herein, "cancer" refers to all types of cancer or neoplasm or malignant tumors found in mammals, including carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that compound that tests positive in the P388 assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with pyridinylimidazole carbamate and optionally a potentiator and/or chemotherapeutic agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with pyridinylimidazole carbamate and optionally a potentiator and/or another chemotherapeutic agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with pyridinylimidazole carbamate and optionally a potentiator and/or a chemotherapeutic agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hürthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with pyridinylimidazole carbamate according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

As used herein, the "pyridinylimidazole carbamate" or "pyridinylimidazole carbamate compound" are used interchangeably to mean those chemicals having the formula:

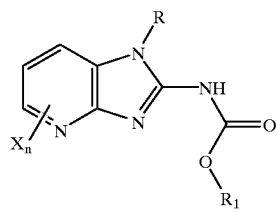

wherein X is independently selected from the group consisting of halo, for example, bromo, fluoro, chloro, iodo; hydroxyl, alkyl of less than 8 carbon atoms or alkoxy of less than 8 carbon atoms; n is a positive integer less than 4; and R and $R_1$ are independently selected from hydrogen or an alkyl group of from 1 to 8 carbons and its pharmaceutically acceptable salts and prodrugs thereof. Preferably R is hydrogen and $R_1$ is an alkyl group of less than 3 carbon atoms. More specific pyridinylimidazole carbamates are described in detail below.

By "alkyl" as used herein is meant a straight, branched or cyclic alkane derivatives. Preferably the alkyl is methyl or ethyl. While tert-butyl is a preferred alkyl, it is generally not present as more than one substituent due to its size.

As used herein "combination therapy" or "adjunct therapy" means that the patient in need of the drug is treated or given another drug for the disease in conjunction with the pyridinylimidazole carbamate. This combination therapy can be sequential therapy where the patient is treated first with one drug and then the other or the two drugs are given simultaneously.

B. The Pyridinylimidazole Carbamate

The compounds have the following structure:

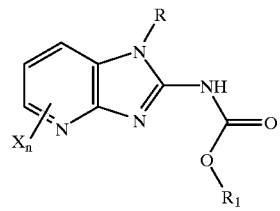

wherein X is independently selected from the group consisting of halo, for example, bromo, fluoro, chloro, iodo; hydroxyl, alkyl of less than 8 carbon atoms or alkoxy of less than 8 carbon atoms; n is a positive integer less than 4; and R and $R_1$ are independently selected from the group of hydrogen or an alkyl group of from 1 to 8 carbons and pharmaceutically acceptable salts and prodrugs thereof. Preferably $R_1$ is an alkyl group of less than 3 carbon atoms and R is hydrogen.

The pyridinylimidazole carbamate compounds also include prodrugs. "Prodrugs" are considered to be any covalently bonded carriers which release the active parent drug according to the formula of the pyridinylimidazole carbamate described above in vivo when such prodrug is administered to a mammalian subject. Prodrugs of the pyridinylimidazole carbamate compound are prepared by modifying functional groups present in the compounds in such a way that the modifications are cleaved, either in routine manipulation or in vivo, to the parent compounds. Prodrugs include compounds wherein amine or hydroxyl groups are bonded to any group that, when administered to a mammalian subject, cleaves to form a free amino or hydroxyl group, respectively. Examples of prodrugs include, but are not limited to, acetate, formate, or benzoate derivatives of amine or hydroxyl functional groups in the pyridinylimidazole carbamates; and the like. Aryl sulfonates, e.g. p-tolunesulfonates of hydroxyl which would hydrolyze to the free hydroxyl in the body.

The pharmaceutically acceptable salts of the pyridinylimidazole carbamate includes the conventional non-toxic salts or the quaternary ammonium salts of the pyridinylimidazole carbamate formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention are synthesized from the pyridinylimidazole carbamate which contain a basic moiety by conventional chemical methods. Generally, such salts are prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418.

Synthesis

The pyridinylimidazole carbamate is prepared in a number of ways well known to one skilled in the art of organic synthesis. They can be synthesized by starting with a substituted 2,3-diaminopyridine. This compound is then converted to the pyridinylimidazole carbamate by cyclizing with isothiourea reagent. Isothiourea is prepared from 2-methyl-2-thiopseudourea sulfate and methyl chloroformate by reaction in a water-dichloromethane system under phase transfer conditions. This method is illustrated for the synthesis below.

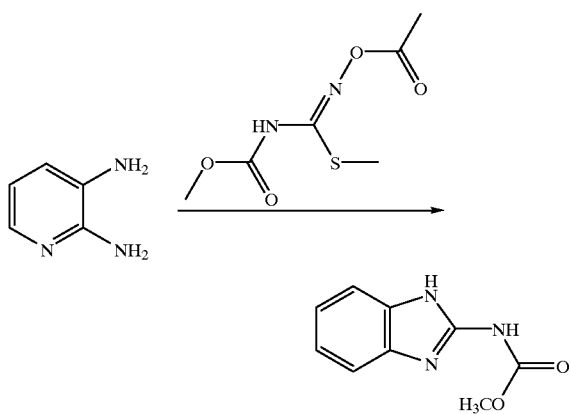

The isothiourea reagent can be substituted to produce different substituent groups on the carbamate portion of the compound. The diaminopyridine can also be a substituted pyridine, for example, 3-methyl -1, 2-diaminopryidine.

See for example, the following references which describe methods of synthesis of pyridinylimidazole carbamates.

Berthold, et al, U.S. Pat. No. 3,590,045 (1971);

Boesch, GB 1,318,859 (1971)

One skilled in the art of organic synthesis can modify these reaction to make other compounds used herein.

C. Combination Therapy

In some embodiments, pyridinylimidazole carbamate is used in combination with one or more potentiators and/or chemotherapeutic agents for the treatment of cancer or tumors. These combinations can be administered together or sequentially.

An exemplary potentiator is triprolidine or its cis-isomer which are used in combination with chemotherapeutic agents and pyridinylimidazole carbamates. Triprolidine is described in U.S. Pat. No. 5,114,951 (1992). Another potentiator is procodazole, 1H-Benzimidazole carbamate-2-propanoic acid; [β-(2-benzimidazole carbamate) propionic acid; 2-(2-carboxyethyl)benzimidazole carbamate; propazol]. Procodazole is a non-specific immunoprotective agent active against viral and bacterial infections that is used with the compositions claimed herein. It is effective with pyridinylimidazole carbamate in treating cancers, tumors or leukemia. Procodazole can also be combined with pyridinylimidazole carbamate and other chemotherapeutic agents to treat cancer, tumor or leukemia.

Other potentiators which can be used with pyridinylimidazole carbamate and optionally another chemotherapeutic agent to treat or inhibit the growth of cancer include monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, leucovorin, heparin, N-[4-[(4-fluorphenyl)sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

The chemotherapeutic agents which can be used with pyridinylimidazole carbamate and an optional potentiator are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with pyridinylimidazole carbamate includes members of all of these groups. For a detailed discussion of chemotherapeutic agents and their method of administration, see Dorr, et al, *Cancer Chemotherapy Handbook*, 2d edition, pages 15–34, Appleton & Lange (Connecticut, 1994).

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposde; and the DNA minor groove binder Plicamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa;

methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine.

DNA strand breaking agents include Bleomycin.

DNA topoisomerase II inhibitors include the following:

Intercalators, such as Amsacrine, Dactinomycin, Daunorubicin, Doxorubicin, Idarubicin, and Mitoxantrone; and nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine and Floxuridine purine antagonists such as Mercaptopurine, 6-Thioguanine, Pentostatin;

sugar modified analogs such as Cytarabine and Fludarabine; and ribonucleotide reductase inhibitors such as hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include colchicine, Vincristine and Vinblastine, both alkaloids and Paclitaxel and cytoxan.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol; and androgens such as testosterone, testosterone propionate; fluoxymesterone, methyltestosterone.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamoxifen, antiandrogen agents such as Flutamide; and antiadrenal agents such as Mitotane and Aminoglutethimide.

Hydroxyurea, which appears to act primarily through inhibition of the enzyme ribonucleotide reductase, can also be used in combination with pyridinylimidazole carbamates.

Asparaginase is an enzyme which converts asparagine to nonfunctional aspartic acid and thus blocks protein synthesis in the tumor. Asparaginase can also be used in combination with pyridinylimidazole carbamate to treat cancer.

D. Dosage

Pyridinylimidazole carbamate is preferably micronized or powdered so that it is more easily dispersed and solubilized by the body. Processes for grinding or pulverizing drugs are well known in the art. For example, a hammer mill or similar milling device are used. The preferred particle size is less than about 100μ and preferably less than 50 μ.

Dosage forms (compositions) suitable for internal administration contain from about 1.0 milligram to about 5000 milligrams of active ingredient per unit. In these pharmaceutical compositions, the active ingredient will ordinarily be present in an amount of about 0.5–95% by weight based on the total weight of the composition. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one pill will provide a dose of 25 mg per kg for that patient. It will provide a dose of only 12.5 mg/kg for a 80 kg patient.

Pyridinylimidazole carbamate exhibits efficacy in vivo against cancers in mice at doses of about 1000 mg/kg, 2000 mg/kg and 4000 mg/kg. Generally, an effective dose in mice is about 12 times the expected effective dose in humans. By way of general guidance, for humans a dosage of as little as about 25 milligrams (mg) per kilogram (kg) of body weight and up to about 10000 mg per kg of body weight is suitable as a therapeutically effective dose. Preferably, from about 40 mg/kg to about 2500 mg/kg of body weight is used. Other preferred doses range between 100 mg/kg to about 3000 mg/kg of body weight. However, a dosage of between about 2 milligrams (mg) per kilogram (kg) of body weight to about 400 mg per kg of body weight is also suitable for treating some cancers.

Intravenously, the most preferred rates of administration may range from about 1 to about 1000 mg/kg/minute during a constant rate infusion. Pyridinylimidazole carbamate can be administered in a single daily dose, or the total daily dosage may be administered in divided doses of two, three, or four times daily. Pyridinylimidazole carbamate is generally given in one or more doses on a daily basis or from one to three times a week.

Pyridinylimidazole carbamate is administered by any conventional means available for use in conjunction with pharmaceuticals, either as individual therapeutic agents or in combination with other therapeutic agents The amount and identity of a chemotherapeutic agent that is used with pyridinylimidazole carbamate in treating cancer, tumor, leukemia, or other related diseases will vary according to patient response and physiology, type and severity of side effects, the disease being treated, the preferred dosing regimen, patient prognosis or other such factors.

When pyridinylimidazole carbamate is used in combination with other therapeutic agents, the ratio of pyridinylimidazole carbamate to the other therapeutic agent will be varied as needed according to the desired therapeutic effect, the observed side-effects of the combination, or other such considerations known to those of ordinary skill in the medical arts. Generally, the ratio of pyridinylimidazole carbamate to other therapeutic agent will range from about 0.5%: 99.5% to about 99.5%: 0.5% on a weight basis.

When pyridinylimidazole carbamate is administered before or after other therapeutic agents to treat cancer, tumors, or other diseases, the respective doses and the dosing regimen of pyridinylimidazole carbamate and the other therapeutic agent may vary. The adjunct or combination therapy can be sequential, that is the treatment with one agent first and then the second agent, or it can be concomitant treatment wherein two or more agents are administered substantially at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the disease and the response to the treatment.

For example, a full dosing regimen of pyridinylimidazole carbamate can be administered either before or after a full dosing regimen of the other therapeutic agent, or alternating doses of pyridinylimidazole carbamate and the other therapeutic agent may be administered. As a further example, pyridinylimidazole carbamate can be administered concomitantly with the other therapeutic agent.

The identity of the chemotherapeutic agent, the pharmaceutical carrier and the amount of compound administered will vary widely depending on the species and body weight of mammal and the type of cancer being treated. The dosage administered will vary depending upon known factors, such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

Pyridinylimidazole carbamates, the potentiator and/or the chemotherapeutic agent are administered together in a single dosage form or separately in two or more different dosage forms. These can be administered independently by the same route or by two or more different routes of administration depending on the dosage forms employed.

Suitable pharmaceutical compositions and dosage forms will preferably comprise pyridinylimidazole carbamates, a potentiator and optionally a chemotherapeutic agent. The ratio of pyridinylimidazole carbamate to potentiator is generally in the range of about 1:0.01 to 10:1, and preferably 1:0.05 to 1:1 on a weight basis.

The dose and the range of chemotherapeutic agent will depend on the particular agent and the type of cancer being treated. One skilled in the art will be able to ascertain the appropriate dose.

E. Dosage Form

A dosage unit may comprise a single compound or mixtures thereof with other anti-cancer compounds, other cancer or tumor growth inhibiting compounds. Pyridinylimidazole carbamate can be administered in oral dosage forms as tablets, capsules, pills, powders, granules, elixirs, tinctures, suspensions, syrups, and emulsions. Pyridinylimidazole carbamate may also be administered in intravenous (bolus or infusion), intraperitoneal, subcutaneous, or intramuscular form, all using dosage forms well known to those of ordinary skill in the pharmaceutical arts.

Pyridinylimidazole carbamate is typically administered in admixture with suitable pharmaceutical diluents, extenders, excipients, or carriers (collectively referred to herein as a pharmaceutically acceptable carrier or carrier materials) suitably selected with respect to the intended form of administration and as consistent with conventional pharmaceutical practices. The unit will be in a form suitable for oral, rectal, topical, intravenous injection or parenteral administration.

Pyridinylimidazole carbamate can be administered alone but is generally mixed with a pharmaceutically acceptable carrier. This carrier can be a solid or liquid, and the type of carrier is generally chosen based on the type of administration being used.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modem Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers : Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Pyridinylimidazole carbamate can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Pyridinylimidazole carbamate may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, pyridinylimidazole carbamate may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Pyridinylimidazole carbamate may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Useful pharmaceutical dosage forms for administration of pyridinylimidazole carbamates are illustrated as follows:

Capsules

A large number of unit capsules are prepared by filling standard two-piece hard gelatin capsules each with 10 to 500 milligrams of powdered active ingredient, 5 to 150 milligrams of lactose, 5 to 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100–500 milligrams of the active ingredient. The capsules are washed and dried.

Tablets

A large number of tablets are prepared by conventional procedures so that the dosage unit was 100–500 milligrams of active ingredient, 0.2 milligrams of colloidal silicon dioxide, 5 milligrams of magnesium stearate, 50–275 milligrams of microcrystalline cellulose, 11 milligrams of starch and 98.8 milligrams of lactose. Appropriate coatings may be applied to increase palatability or delay absorption.

Injectable Solution

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Kits

The present invention also includes pharmaceutical kits useful, for example, for the treatment of cancer, which comprise one or more containers containing a pharmaceutical composition comprising a therapeutically effective amount of pyridinylimidazole carbamates. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The chemotherapeutic agents, pyridinylimidazole carbamate and, optionally, the potentiators are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid fonns include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

F. Method of Treatment

The method of treatment can be any suitable method which is effective in the treatment of the particular cancer or tumor type being treated. Treatment may be oral, rectal, topical, parenteral or intravenous administration or by injection into the tumor or cancer. The method of administering an effective amount also varies depending on the disorder or disease being treated. It is believed that parenteral treatment by intravenous, subcutaneous, or intramuscular application of the pyridinylimidazole carbamates, formulated with an appropriate carrier, additional cancer inhibiting compound or compounds or diluent to facilitate application will be the preferred method of administering the compounds to warm blooded animals.

One skilled in the art will recognize that the efficacy of the pyridinylimidazole carbamates can be ascertained through routine screening using known cancer cell lines both in vitro and in vivo. Cell lines are available from American Tissue Type Culture or other laboratories.

The following examples are illustrative and not intended to be limiting of the invention.

EXAMPLE 1

Imidazo [4,5-b]pyridine-2-carbamic acid, methyl ester was used to treat HT29, a colon cancer tumor line, in nude mouse. The average tumor weight is reported in mg. The control was the vehicle given twice a week. The imidazo [4,5-b]pyridine-2-carbamic acid, methyl ester was also given on this same schedule. Both compounds were administered by oral gavage.

| Compound | Average Tumor Weight on Day | | | | | | | | | | | | | | | | |
|---|---|---|---|---|---|---|---|---|---|---|---|---|---|---|---|---|---|
| | 1 | 5 | 8 | 11 | 15 | 18 | 23 | 26 | 30 | 33 | 37 | 40 | 44 | 47 | 51 | 54 | 58 |
| Control PEG | 76.4 | 110.1 | 147.9 | 228 | 307.5 | 410.1 | 544.2 | 674.2 | 893.5 | 767.4 | 915.9 | 824.8 | 964.3 | — | — | — | — |
| Pyridnyl-1000 mg/kg p.o. | 75.4 | 97.2 | 138.2 | 172.1 | 220.1 | 281.6 | 340.6 | 407.6 | 515.6 | 562 | 828.3 | 533.7 | 714.4 | 656.8 | 763.6 | 793.3 | 919 |
| pyridinyl- 1500 m/kg p.o. | 76.6 | 76.1 | 94.4 | 130 | 166.3 | 189.3 | 242.3 | 264 | 405 | — | — | — | — | — | — | — | — |
| pyridinyl-2500 mg/kg p.o. | 76.2 | 62.6 | 115.2 | 101.1 | 196 | 126 | 256 | 171.5 | — | — | — | — | — | — | — | — | — |

What is claimed is:

1. A method of treating cancer comprising administering to a patient in need thereof a therapeutically effective amount of a composition comprising a pyridinylimidazole carbamate of the formula:

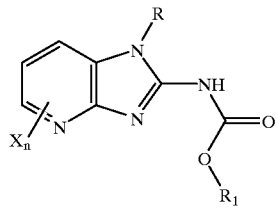

wherein
X is independently selected from the group consisting of hydrogen halo, hydroxyl, alkyl of less than 8 carbon atoms and alkoxy of less than 8 carbon atoms;
n is a positive integer less than 4; and
R and R₁ are independently selected from hydrogen, or an alkyl group of from 1 to 8 carbons,
or a pharmaceutically acceptable salt thereof, or a prodrug thereof.

2. A method according to claim 1 wherein said cancer is prostate cancer.

3. A method according to claim 1 wherein said cancer is breast cancer.

4. A method according to claim 1 wherein said cancer is colon cancer.

5. A method according to claim 1 wherein said cancer is lung cancer.

6. A method according to claim 1 wherein said cancer is pancreatic cancer.

7. A method according to claim 1 wherein said cancer is ovarian cancer.

8. A method according to claim 1 wherein said cancer is a sarcoma.

9. A method according to claim 1 wherein said cancer is a lymphoma.

10. A method according to claim 1 wherein said pyridinylimidazole carbamate is

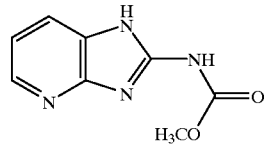

or a pharmaceutically acceptable acid salt or a prodrug thereof.

11. A method according to claim 10 wherein said pharmaceutically acceptable salt is a hydrochloride salt.

12. A method of treating cancer comprising administering to a patient in need thereof a therapeutically effective amount of a combination therapy comprising (1) a pyridinylimidazole carbamate of the formula:

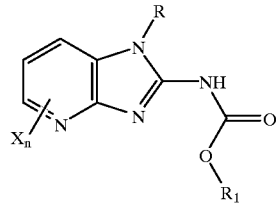

wherein
X is selected from the group consisting of hydrogen, bromo, fluoro, chloro, iodo, alkyl of less than 7 carbon atoms and alkoxy of less than 7 carbon atoms;
n is a positive integer less than 4;
R is hydrogen or an alkyl group of from 1 to 8 carbon atoms; and
R₁ is aliphatic hydrocarbon of less than 7 carbon atoms or a pharmaceutically acceptable salt or prodrug thereof and (2) a safe and effective amount of another chemotherapeutic agent.

13. A method according to claim 12 wherein said cancer is prostate cancer.

14. A method according to claim 12 wherein said cancer is ovarian cancer.

15. A method according to claim 12 wherein said cancer is pancreatic cancer.

16. A method according to claim 12 wherein said cancer is breast cancer.

17. A method according to claim 12 wherein said cancer is lung cancer.

18. A method according to claim 12 wherein said cancer is colon cancer.

19. A method according to claim 12 wherein said pyridinylimidazole carbamate has the formula:

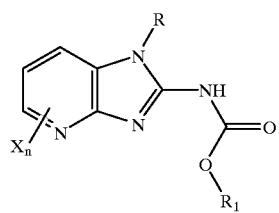

wherein

X is hydrogen;

n is a positive integer less than 4; and

R and $R_1$ are hydrogen or an alkyl group of from 1 to 4 carbons.

20. A method according to claim 19 wherein said chemotherapeutic agent is selected from the group consisting of a DNA-interactive agent, alkylating agent, antimetabolite, tubulin-interactive agent, hormonal agent, Asparaginase and hydroxyurea.

21. A method according to claim 19 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole carbamate and Plicamycin.

22. A method according to claim 19 wherein said chemotherapeutic agent is selected from the group consisting of Methotrexate, Fluorouracil, Fluorodeoxyuridine, CB3717, Azacitidine, Floxuridine, Mercaptopurine, 6-Thioguanine, Pentostatin, Cytarabine, and Fludarabine.

23. A method according to claim 19 further comprising a safe and effective amount of a potentiator.

24. A method according to claim 23, wherein said potentiator is selected from the group consisting of procodazole, triprolidine, propionic acid, monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl) ethylenediamine, N-[4-[(4-fluorphenyl)sulfonly]phenyl] acetamide, leucovorin, heparin, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

* * * * *

UNITED STATES PATENT AND TRADEMARK OFFICE
CERTIFICATE OF CORRECTION

PATENT NO.   : 6,384,049 B1
DATED        : May 7, 2002
INVENTOR(S)  : James B. Camden It is certified that error appears in the above-identified patent and that said Letters Patent is hereby corrected as shown below:

<u>Column 15,</u>
Line 32, insert a comma -- , -- immediately after "hydrogen".

Signed and Sealed this

Third Day of December, 2002

JAMES E. ROGAN
*Director of the United States Patent and Trademark Office*